United States Patent [19]

Pi Subirana et al.

[11] Patent Number: 5,869,716
[45] Date of Patent: Feb. 9, 1999

[54] PROCESS FOR THE PRODUCTION OF ESTERQUATS

[75] Inventors: Rafael Pi Subirana, Granollers; Joaquim Bigorra Llosas, Sabadell; Antonio Trius Oliva, Valldoreix, all of Spain

[73] Assignee: Henkel Kommanditgesellschaft auf Aktien, Duesseldorf, Germany

[21] Appl. No.: 704,694

[22] PCT Filed: Mar. 9, 1995

[86] PCT No.: PCT/EP95/00861

§ 371 Date: Sep. 16, 1996

§ 102(e) Date: Sep. 16, 1996

[87] PCT Pub. No.: WO95/25713

PCT Pub. Date: Sep. 28, 1995

[51] Int. Cl.[6] .................................................. C07C 227/00
[52] U.S. Cl. .......................... 554/114; 554/103; 554/107; 564/281; 564/291; 564/296
[58] Field of Search ..................... 554/103, 107, 554/114; 564/281, 291, 296

[56] References Cited

U.S. PATENT DOCUMENTS 3,915,867  10/1975  Kang et al. ............................... 252/8.8
4,370,272  1/1983   Wechsler et al. ........................ 260/404
5,437,801  8/1995   Lüders et al. ............................ 252/8.8

FOREIGN PATENT DOCUMENTS 239 910   10/1987  European Pat. Off. .
293 955   12/1988  European Pat. Off. .
295 739   12/1988  European Pat. Off. .
309 052    3/1989  European Pat. Off. .
498 050    8/1992  European Pat. Off. .
525 271    2/1993  European Pat. Off. .
550 361    7/1993  European Pat. Off. .
91/01295   2/1991  WIPO .

OTHER PUBLICATIONS

O. Ponsati, C.R.CED Congress, Barcelona, 1992, p. 167.
R. Puchta, et al.,C.R. CED Congress, Sitges, 1993, p. 59.

*Primary Examiner*—Gary Geist
*Assistant Examiner*—Deborah D. Carr
*Attorney, Agent, or Firm*—Wayne C. Jaeschke; John E. Drach; Steven J. Trzaska

[57] ABSTRACT

Esterquats based on natural fats and oils can be directly produced by subjecting fatty acid glyerine ester to ester interchange, in the presence of alkaline and/or alkaline earth boron hydrides and hypophosphoric acid or their alkaline and/or alkaline earth salts and possibly free fatty acid, with hydroxy-functionalised tertiary amines and quaternising the resultant products in the manner known per se.

14 Claims, No Drawings

PROCESS FOR THE PRODUCTION OF ESTERQUATS

This application is a 371 of PCT/EP 95/00861 filed May 9, 1995.

BACKGROUND OF THE INVENTION

1. Field of the Invention

This invention relates to a process for the production of esterquats, in which fatty acid glycerol esters are directly transesterified with tertiary hydroxyamines and then quaternized, and to the use of the products for the production of surface-active formulations.

2. Statement of Related Art

In recent years, quaternized fatty acid triethanolamine ester salts, socalled "esterquats", have acquired increasing significance as ecotoxicologically safe raw materials for fabric softeners [cf. O. Ponsati in C.R. CED Congress, Barcelona, 167 (1992) and R. Puchta in C.R. CED Congress, Sitges, 59 (1993)].

According to the teaching of International patent application WO 91/01295 (Henkel), esterquats are normally produced from triethanolamine or adducts of ethylene oxide with triethanolamine which, in a first step, are partly esterified with linear $C_{16/18}$ fatty acids in the presence of hypophosphorous acid and subsequently treated with air. The fatty acid triethanolamine esters are then quaternized, for example with alkyl halides or, preferably, dialkyl sulfates.

Instead of fatty acids themselves, it is desirable for economic reasons directly to use natural fats and oils, from which the fatty acids are obtained, as starting materials for the production of esterquats. However, according to studies conducted by applicants, application of this principle on an industrial scale has hitherto been prevented by the fact that transesterification in the presence of the alkaline catalysts typically used for this type of reaction, namely potassium hydroxide or sodium methylate, generally involves overly long reactor possession times and, in general, leads to discolored products which have to be bleached in an additional, expensive process step.

Accordingly, the problem addressed by the present invention was to provide a process for the production of esterquats based on fats and oils as starting materials which would not have any of the disadvantages mentioned above.

DESCRIPTION OF THE INVENTION

The present invention relates to a process for the production of esterquats in which fatty acid glycerol esters are subjected to transesterification with hydroxyfunctionalized tertiary amines in the presence of alkali metal and/or alkaline earth metal borohydrides and hypophosphorous acid or alkali metal and/or alkaline earth metal salts thereof and, optionally, free fatty acid and the resulting products are quaternized in known manner.

It has surprisingly been found that the use of borohydrides as opposed to other conventional transesterification catalysts leads to a quick and complete reaction which, in addition, gives reaction products that are distinguished by particularly high color quality. In addition, the process according to the invention affords the advantage that fats and oils can be directly used instead of fatty acids which increases the economy of the process.

Esterquats

Esterquats are generally understood to be quaternized fatty acid triethanolamine ester salts. These are known substances which may be obtained by the relevant methods of preparative organic chemistry, cf. International patent application WO 91/01295 (Henkel). According to this document, triethanolamine is partly esterified with fatty acids in the presence of hypophosphorous acid, air is passed through and the fatty acid triethanolamine esters are subsequently quaternized with dimethyl sulfate or ethylene oxide. U.S. Pat. No. 3,915,867, U.S. Pat. No. 4,370,272, EP-A2 0 239 910, EP-A2 0 293 955, EP-A2 0 295 739 and EP-A2 0 309 052 are cited at this juncture as representative of the extensive prior art on this subject.

The quaternized fatty acid triethanolamine ester salts correspond to formula (I):

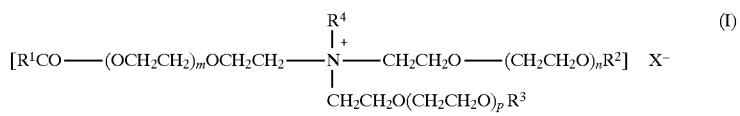

in which $R^1CO$ is an acyl radical containing 6 to 22 carbon atoms, $R^2$ and $R^3$ independently of one another represent hydrogen or have the same meaning as $R^1CO$, $R^4$ is an alkyl radical containing 1 to 4 carbon atoms or a $(CH_2\text{—}CH_2O)_qH$ group, m, n and p have a combined value of 0 or 1 to 12, q is a number of 1 to 12 and X is halide, alkyl sulfate or alkyl phosphate.

Typical examples of esterquats which may be used in accordance with the invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained, for example, in the pressure hydrolysis of natural fats and oils. Technical $C_{12/18}$ cocofatty acids and, in particular, partially hydrogenated $C_{16/18}$ tallow or palm oil fatty acid and also $C_{16/18}$ fatty acid cuts rich in elaidic acid are preferably used.

Quaternized fatty acid triethanolamine ester salts corresponding to formula (I), in which $R^1CO$ is an acyl radical containing 16 to 18 carbon atoms, $R^2$ has the same meaning as $R^1CO$, $R^3$ is hydrogen, $R^4$ is a methyl group, m, n and p have a combined value of 0 and X stands for methyl sulfate, have proved to be particularly advantageous from the performance point of view.

Besides the quaternized fatty acid triethanolamine ester salts, other suitable esterquats are quaternized ester salts of fatty acids with diethanol alkylamines corresponding to formula (II):

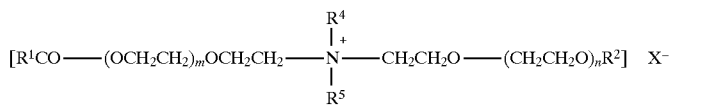

in which $R^1CO$ is an acyl radical containing 6 to 22 carbon atoms, $R^2$ is hydrogen or has the same meaning as $R^1CO$, $R^4$ and $R^5$ independently of one another represent alkyl radicals containing 1 to 4 carbon atoms, m and n have a combined value of 0 or 1 to 12 and X stands for halide, alkyl sulfate or alkyl phosphate.

Finally, another group of suitable esterquats are the quaternized ester salts of fatty acids with 1,2-dihydroxypropyl dialkylamines corresponding to formula (III):

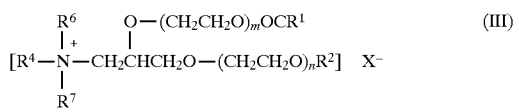

in which $R^1CO$ is an acyl radical containing 6 to 22 carbon atoms, $R^2$ is hydrogen or has the same meaning as $R^1CO$, $R^4$, Re and $R^7$ independently of one another represent alkyl radicals containing 1 to 4 carbon atoms, m and n have a combined value of 0 or 1 to 12 and X stands for halide, alkyl sulfate or alkyl phosphate.

So far as the choice of preferred fatty acids is concerned, the examples mentioned for (I) also apply to the esterquats of formulae (II) and (III).

Fatty acid glycerol esters

Fatty acid glycerol esters in the context of the invention are synthetic or preferably natural triglycerides, diglycerides, monoglycerides or technical mixtures thereof. The glycerol esters generally contain fatty acids with 6 to 22 and preferably 12 to 18 carbon atoms. They may be saturated or may contain up to 3 double bonds. In addition, the glycerol esters may contain one type of fatty acid or up to three different fatty acids. Typical examples of triglycerides which may be used in the process according to the invention are palm oil, palm kernel oil, coconut oil, olive oil, rapeseed oil from old and new plants, sunflower oil from old and new plants, cottonseed oil, linseed oil, peanut oil, beef tallow and lard. From the performance point of view, it is preferred to use completely or partly hydrogenated beef tallow or palm oil with iodine values in the range from 0 to about 50.

Hydroxyfunctionalized tertiary amines

In the transesterification reaction, at least one fatty acid of the glyceride reacts with one OH group of a hydroxyfunctionalized tertiary amine. Typical examples of suitable amines are diethanol alkylamines such as, for example, diethanol methylamine and 1,2-dihydroxypropyl dialkylamines such as, for example, 1,2-dihydroxypropyl dimethylamine and, in particular, triethanolamine.

The fatty acid glycerol esters—expressed on the basis of the fatty acids present in them—and the amines may be used in a molar ratio of around 1.2:1 to 2.2:1 and preferably 1.4:1 to 1.9:1.

Catalysts

Alkali metal and/or alkaline earth metal borohydrides may be used as the transesterification catalysts. Typical examples are potassium or magnesium borohydride and preferably sodium borohydride. The catalysts are normally used in quantities of 50 to 1000 ppm and preferably in quantities of 100 to 500 ppm, based on the glycerol ester.

Suitable co-catalysts are hypophosphorous acid and alkali metal and/or alkaline earth metal salts thereof, preferably sodium hypophosphite, used in quantities of 0.01 to 0.1% by weight and preferably in quantities of 0.05 to 0.07% by weight, based on the glycerol ester.

Fatty acids

In one preferred embodiment of the process according to the invention, the transesterification reaction takes place in the presence of free fatty acids containing 6 to 22 and preferably 12 to 18 carbon atoms which may be used in quantities of 1 to 5% by weight and, more particularly, 2 to 3% by weight, based on the glycerol ester. Typical examples of suitable fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or in the reduction of aldehydes from Roelen's oxosynthesis.

Technical fatty acids containing 12 to 18 carbon atoms, for example coconut oil, palm oil, palm kernel oil or tallow fatty acid, which correspond to the fatty acid of the triglyceride used are preferred.

Transesterification

The transesterification is normally carried out over a period of 1 to 12 hours and preferably 3 to 6 hours at temperatures in the range from 160° to 240° C. and preferably at temperatures in the range from 180° to 220° C.

Quaternization

The fatty acid hydroxyalkylamine esters and the quaternizing agents may be used in a molar ratio of 1:0.95 to 1:1.2 and preferably in a molar ratio of 1:1 to 1:1.1 in the quaternization reaction. Suitable alkylating agents are alkyl halides, for example methyl chloride, dialkyl sulfates, for example dimethyl sulfate, dialkyl phosphates and dialkyl carbonates, for example dimethyl carbonate or diethyl carbonate. The reaction usually takes place in a solvent, for example a lower alcohol (isopropyl alcohol), a fatty alcohol (ceteareth alcohol), a nonionic surfactant (alkyl oligoglucoside, adducts of ethylene oxide with fatty alcohols or partial glycerides) or a hydroxycarboxylic acid (glycolic acid). The quaternization is preferably carried out at temperatures of 70° to 100° C. and, more particularly, at temperatures of 80° to 90° C. The reaction time may be between 1 and 24 h and is preferably between 2 and 8 h. After the quaternization, it is advisable to destroy unreacted alkylating agent by addition of ammonia, glycine or monoethanolamine.

Commercial Applications

The esterquats obtainable by the process according to the invention are distinguished by excellent fabric-softening and antistatic properties.

Accordingly, the present invention also relates to their use for the production of fabric softeners and hair-care formulations, such as softeners for textiles, yarns and fibers, household fabric softeners, hair shampoos, hair conditioners, hair rinses and the like, in which they may be present in quantities of 1 to 30% by weight and preferably in quantities of 5 to 15% by weight, based on the particular formulation.

The following Examples are intended to illustrate the invention without limiting it in any way.

EXAMPLES

General production procedure a) Esterification. 0.4 to 0.63 mole of triglyceride (corresponding to 1.2 to 1.9 mole, based on fatty acid), 149 g (1 mole) of triethanolamine, 0.05% by weight of sodium hypophosphite, 100 to 500 ppm of catalyst and, optionally, 2.7% by weight of tallow fatty acid (all percentages by weight based on the triglyceride) were introduced into a 1 liter three-necked flask equipped with a stirrer, internal thermometer and distillation head. The reaction mixture was heated for 5 h to a temperature of 220° C. The crude tallow fatty acid triethanolamine ester was then cooled, the reactor was vented and 1 liter of air was passed through over a period of 15 minutes with continuous stirring.

The results of the esterification tests are set out in Table 1.

b) Quaternization. In a 1.5 liter glass autoclave equipped with a stirrer and internal thermometer, 63 g (0.5 mole) of dimethyl sulfate were added to 0.5 mole of the ester according to a) in 150 ml of isopropyl alcohol. The reaction mixture was stirred for 2 h at 90° C. and, after cooling, the reactor was vented. To destroy traces of unreacted alkylating agent, 2 g of glycine were then added to the reaction mixture, followed by stirring for 1 h at 60° C.

TABLE 1

Transesterification of Triglycerides

| Ex. | E | R | Cat | c (Cat) ppm | c (FA) % by weight | t h | Color Gardner |
|---|---|---|---|---|---|---|---|
| 1 | A | 1.2:1 | NaBH$_4$ | 100 | 2.7 | 4 | 1.0 |
| 2 | A | 1.6:1 | NaBH$_4$ | 100 | 2.7 | 4 | 1.2 |
| 3 | A | 1.9:1 | NaBH$_4$ | 100 | 2.7 | 4 | 1.5 |
| 4 | A | 1.9:1 | NaBH$_4$ | 500 | 2.7 | 4 | 1.0 |
| 5 | A | 1.9:1 | NaBH$_4$ | 100 | — | 4 | 1.5 |
| 6 | B | 1.9:1 | NaBH$_4$ | 100 | 2.7 | 4 | 1.5 |
| 7 | C | 1.9:1 | NaBH$_4$ | 100 | 2.7 | 4 | 1.5 |
| C1 | A | 1.9:1 | KOH | 100 | 2.7 | 6 | 3.5 |
| C2 | A | 1.9:1 | NaOMe | 100 | 2.7 | 7 | 3.5 |

Legend:
E = Educt
A = Hydrogenated beef tallow
B = Partly hydrogenated beef tallow
C = Palm oil
R = Ratio of fatty acid (in the triglyceride) to triethanolamine
Cat = Catalyst
FA = Fatty acid (corresponding to the triglyceride)
c = Concentration
t = Time required to establish an acid value < 5

What is claimed is:

1. A process for producing an esterquat comprising the steps of: (1) reacting a fatty acid glycerol ester and a hydroxyfunctionalized tertiary amine in the presence of a catalyst selected from the group consisting of an alkali metal borohydride, an alkaline earth metal borohydride, and a combination thereof; (2) reacting the product of step (1) with a quaternizing agent.

2. The process of claim 1 wherein said esterquat is a compound of the formula (I):

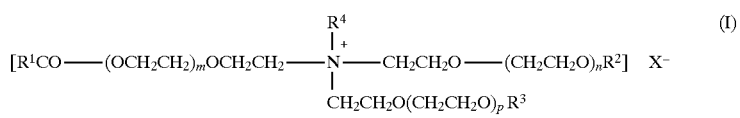

wherein $R^1CO$ is an acyl radical having from 6 to about 22 carbon atoms, each of $R^2$ and $R^3$ is hydrogen or $R^1CO$ as defined above, $R^4$ is an alkyl radical having from 1 to 4 carbon atoms or a $(CH_2CH_2O)_qH$ group; wherein m, n and p are numbers having a sum of from 0 to 12; q is a number from 1 to 12 and X is a halide, an alkyl sulfate or an alkyl phosphate anion.

3. The process of claim 1 wherein said esterquat is a compound of the formula (II):

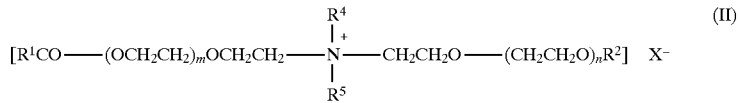

wherein $R^1CO$ is an acyl radical having from 6 to about 22 carbon atoms, $R^2$ is hydrogen or $R^1CO$ as defined above, each of $R^4$ and $R^5$ is an alkyl radical having from 1 to 4 carbon atoms, m and n are numbers having a sum of from 0 to 12 and X is a halide, an alkyl sulfate or an alkyl phosphate anion.

4. The process of claim 1 wherein said esterquat is a compound of the formula (III)

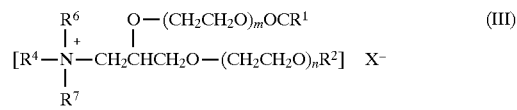

wherein $R^1CO$ is an acyl radical having from 6 to about 22 carbon atoms, $R^2$ is hydrogen or $R^1CO$ as defined above, each of $R^4$, $R^6$ and $R^7$ is an alkyl radical having from 1 to 4 carbon atoms, m and n are numbers having a sum of from 0 to 12 and X is a halide, an alkyl sulfate or an alkyl phosphate anion.

5. The process of claim 1 wherein said fatty acid glycerol ester is a triglyceride, a diglyceride, a monoglyceride or a technical mixture thereof.

6. The process of claim 1 wherein said fatty acid glycerol ester is a completely or partly hydrogenated beef tallow, a palm oil having an iodine value of 0 to about 50.

7. The process of claim 1 wherein said hydroxyfunctionalized tertiary amine is triethanolamine, diethanol alkylamine, 1,2-dihydroxypropyl dialkylamine or a combination thereof.

8. The process of claim 1 wherein the molar ratio of amine to fatty acid in said fatty acid glycerol ester is from about 1.2:1 to about 2.2:1.

9. The process of claim 1 wherein said catalyst is sodium borohydride.

10. The process of claim 1 wherein the amount of said catalyst is from about 50 to about 1000 ppm by weight of said glycerol ester.

11. The process of claim 1 wherein the amount of said catalyst is from about 0.01 to about 0.1% by weight of said glycerol ester.

12. The process of claim 1 wherein the amount of said catalyst is from about 1% to about 5% by weight of said glycerol ester.

13. The process of claim 1 wherein step (1) is carried out over a period of from about 1 to about 12 hours at a temperature of from about 120° to about 180° C.

14. The process of claim 1 wherein said quaternizing agent is an alkyl halide, a dialkyl sulfate, a dialkyl phosphate and a dialkyl carbonate.

* * * * *